(12) United States Patent
Kim et al.

(10) Patent No.: US 7,960,776 B2
(45) Date of Patent: Jun. 14, 2011

(54) TRANSISTOR WITH FLOATING GATE AND ELECTRET

(75) Inventors: Myongseob Kim, Pleasanton, CA (US); Nick Yu-Min Shen, Hsin-Chu County (TW); Chungho Lee, Ithaca, NY (US); Edwin Chihchuan Kan, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 561 days.

(21) Appl. No.: 11/862,867

(22) Filed: Sep. 27, 2007

(65) Prior Publication Data

US 2008/0094074 A1    Apr. 24, 2008

Related U.S. Application Data

(60) Provisional application No. 60/847,516, filed on Sep. 27, 2006.

(51) Int. Cl.
*H01L 29/76* (2006.01)
(52) U.S. Cl. ......... 257/314; 257/315; 257/316; 257/253
(58) Field of Classification Search ........... 257/314–317
See application file for complete search history.

(56) References Cited

U.S. PATENT DOCUMENTS

| | | | |
|---|---|---|---|
| 4,851,682 A | 7/1989 | Moriyama et al. | |
| 6,141,243 A | 10/2000 | Aslam et al. | |
| 7,053,439 B2 * | 5/2006 | Kan et al. | 257/315 |
| 7,186,380 B2 * | 3/2007 | Chen et al. | 422/82.01 |
| 7,462,512 B2 * | 12/2008 | Levon et al. | 438/123 |
| 2005/0230271 A1 | 10/2005 | Levon et al. | |
| 2007/0254455 A1 * | 11/2007 | Yamaguchi et al. | 438/455 |

OTHER PUBLICATIONS

Berry, R. B., et al., "Comparison of respiratory event detection by a polyvinylidene fluoride film airflow sensor and a pneumotachograph in sleep apnea patients.", *Chest*, 128(3), (Sep. 2005), 1331-8.
Kressmann, R., et al., "Space-charge Electrets", *IEEE Transactions on Dielectrics and Electrical Insulation*, 3(5), (Oct. 1996), 607-623.

* cited by examiner

*Primary Examiner* — Zandra Smith
*Assistant Examiner* — Paul E Patton
(74) *Attorney, Agent, or Firm* — Schwegman, Lundberg & Woessner P.A.

(57) ABSTRACT

A sensor includes a field effect transistor having a source, drain, a control gate and floating gate, wherein the floating gate has an extended portion extending away from the control gate. A sensing gate is capacitively coupled to the extended portion of the floating gate. A polymer electret sensing coating is electrically coupled to the sensing gate.

11 Claims, 6 Drawing Sheets

TRANSISTOR WITH FLOATING GATE AND ELECTRET

RELATED APPLICATION

This application claims priority to U.S. Provisional Application Ser. No. 60/847,516 (entitled TRANSISTOR WITH FLOATING GATE AND ELECTRET, filed Sep. 27, 2006) which is incorporated herein by reference.

GOVERNMENT FUNDING

This invention was made with Government support under Grant Number ECS-0210743 awarded by the ECS Division of National Science Foundation. The United States Government has certain rights in the invention.

BACKGROUND

Integrated micro-sensors suitable for economical mass production, low power consumption and good field adaptation are of great interest. Previous attempts on chemical, pressure and light sensors with CMOS integration often required specific structure and readout circuits. The linear sensing elements, although easier for noise compensation, pose fundamental limits on the sensitivity and dynamic range trade-offs.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Figure 9:
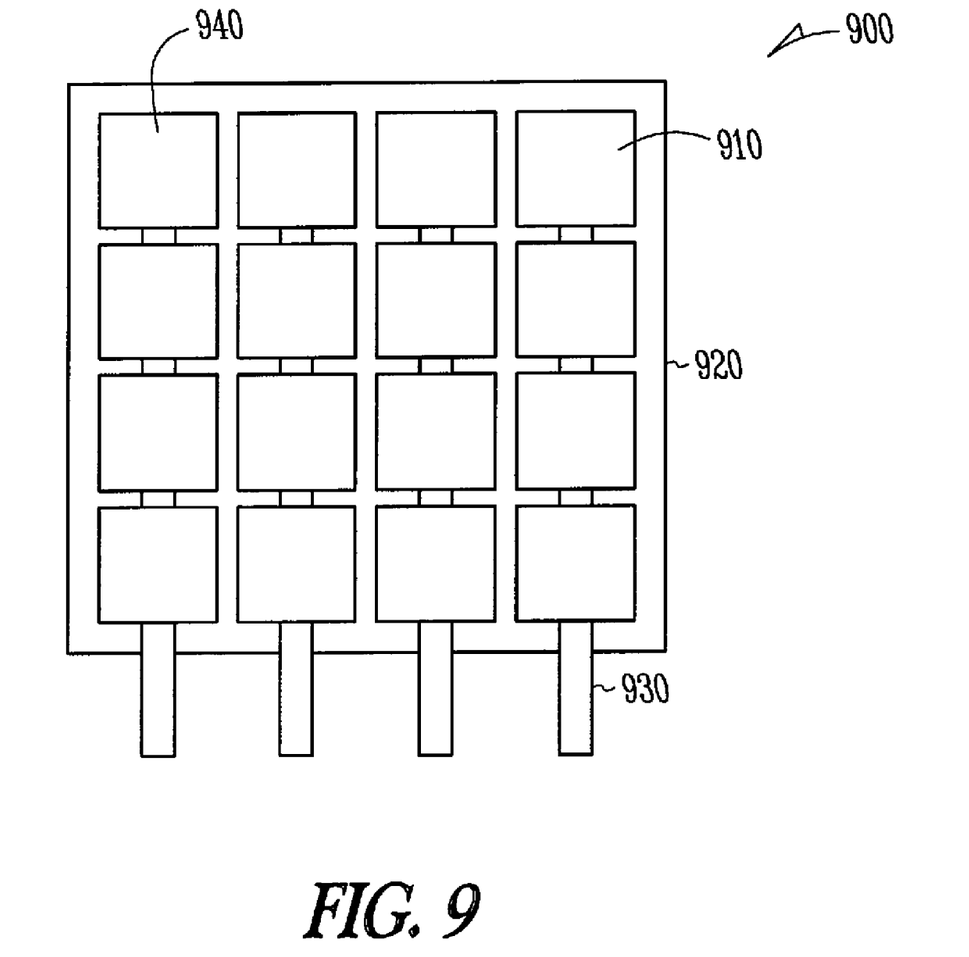
FIG. 9 is a representation of a pixel layout according to an example embodiment.

Charge-base universal sensors for chemicals, molecules, pressure, and light can be mass produced with a simple post processing of the function-specific coating in standard CMOS processes. The various sensors and associated pixel circuits as shown in an array 900 in FIG. 9 may share the same CMOS chip and the specific sensor function is achieved by the post processing coating. Tight integration with CMOS pixel circuits also allows better sensitivity, bandwidth and low power operations. Top metal pixels 910 are in contact with a sense coating 920 in one embodiment. Readout ports 930 provide a mechanism to obtain information about the state of the sense coating in the presence of a desired parameter or parameters to be sensed. In further embodiments, binding wires, such as a metal binding wire illustrated at 940 may be coupled to the metal pixels 910, and then sense coated for applications such as in vivo biomedical sensing. Array 900 may be one dimensional or two dimensional in various embodiments. Even three dimensional arrays may be formed in further embodiments.

In one embodiment, an extended floating gate (FG) of a MOSFET (metal-oxide semiconductor field-effect transistor) is capacitively coupled to a control gate, the MOS channel, and a sensing gate, which can be led out to top metal pixels in physical contact with a post-processing sensing coating. The change in the sensing coating, either as an outer Helmholtz potential ($\phi_{OHP}$), diffusive capacitive load $C_{DIF}$ or effective polarization, will be reflected on nonlinear MOS channel IV curves according to governing equations. A nonlinear drain current gives additional design freedom in the trade-off of sensitivity and dynamic range.

In one embodiment, the sensing coating is a polymer electret film. An electret is a dielectric material exhibiting a quasi-permanent electrostatic charge or charge dipole. The electret charge can be the combination of surface charges, space charges, and charge polarization. There are various methods for forming space-charge and dipolar electrets. For example, space-charge in electrets can be achieved by injecting carriers from discharging or particle beams. Other methods consist of carrier generation within the dielectric by light, radiation or heat with simultaneous charge separation by an electric field. Dipolar electrets can be often obtained by application of a high electric field at room temperature.

In one embodiment, the MOSFET is an EEPROM (Electrically Erasable Programmable Read Only Memory) device with an extended floating gate. The charges in the polymer electret film are capacitively coupled to the floating gate, in the same manner of the conventional control gate directly driven by biases. The polymer electret film sits on a sensing gate electrically isolated from the floating gate by a dielectric. The net charge density in the polymer film weighted by the distance to the sensing gate will influence the potential on the floating gate. Accordingly, the threshold voltage of the EEPROM device at the control gate will change and can be correlated to the electret charge density.

Figure 1:
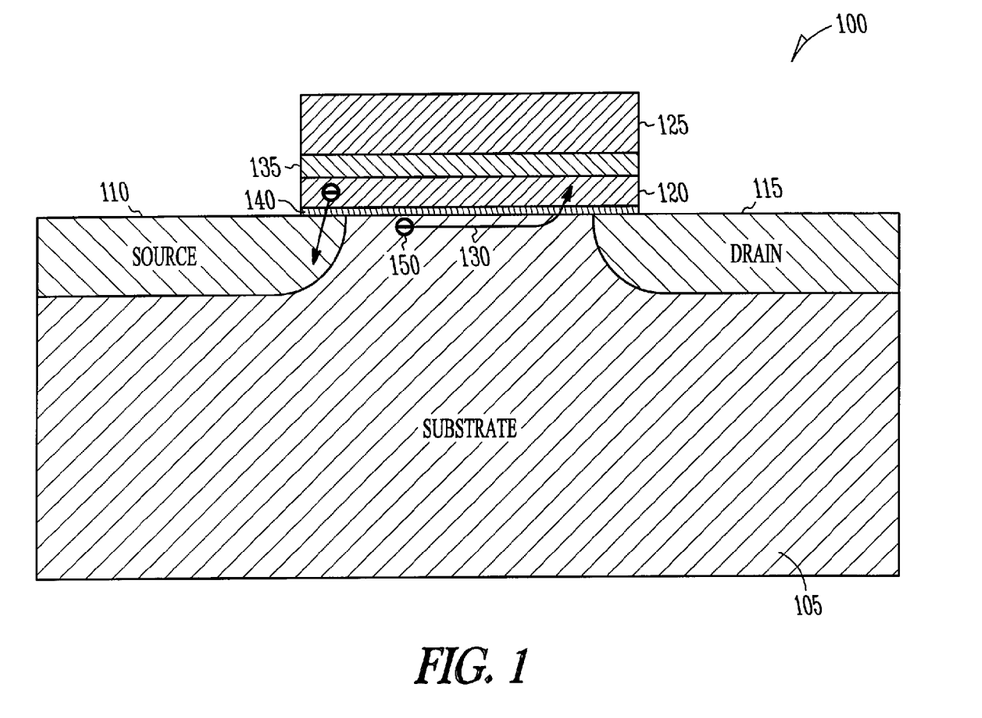
FIG. 1 is a block diagram of an EEPROM structure according to an example embodiment.

FIG. 1 shows a basic EEPROM structure 100 with a substrate 105 having n-type source 110 and drain 115. The device 100 is similar to a traditional MOSFET except that an extra electrically floating conductor layer 120 is sandwiched between the control gate 125 and the channel 130. Oxide or other insulating layers 135 and 140 separate the gate 125, floating gate 120 and channel 130 respectively. The static charge stored in the floating gate 120 has over 10-year lifetime and will influence the threshold voltage of the MOSFET channel 130, which is used to distinguish the stored binary information.

Programming can be implemented by several possible mechanisms. As an example, the channel hot carrier injection is illustrated in FIG. 1, which is performed by applying a high voltage on the control gate 125 (usually around 12V) and drain 115 (~6V) terminals with a grounded source. The substrate 105 is often grounded or further reverse biased to enhance the injection efficiency. During hot-carrier injection, electrons 150 with enough kinetic energy to overcome the oxide energy barrier 140 will be trapped at the floating gate 120. After removing the programming voltages, the trapped negative charges will delay channel inversion, which translates into an effective increase in the MOSFET threshold voltage. To turn on the device during the read operation, a higher control gate voltage is needed to overcome the effect of the floating-gate 120 charges. The erasure operation is performed with the gate 125 grounded and the source 110 at a high voltage, typically also around 12V, when the electrons in the floating gate 120 will leak out through the Fowler-Norhdeim (F-N) tunneling mechanism. Different areas of the gate oxide 140 are used for programming and erasure in this illustration.

Figure 2:
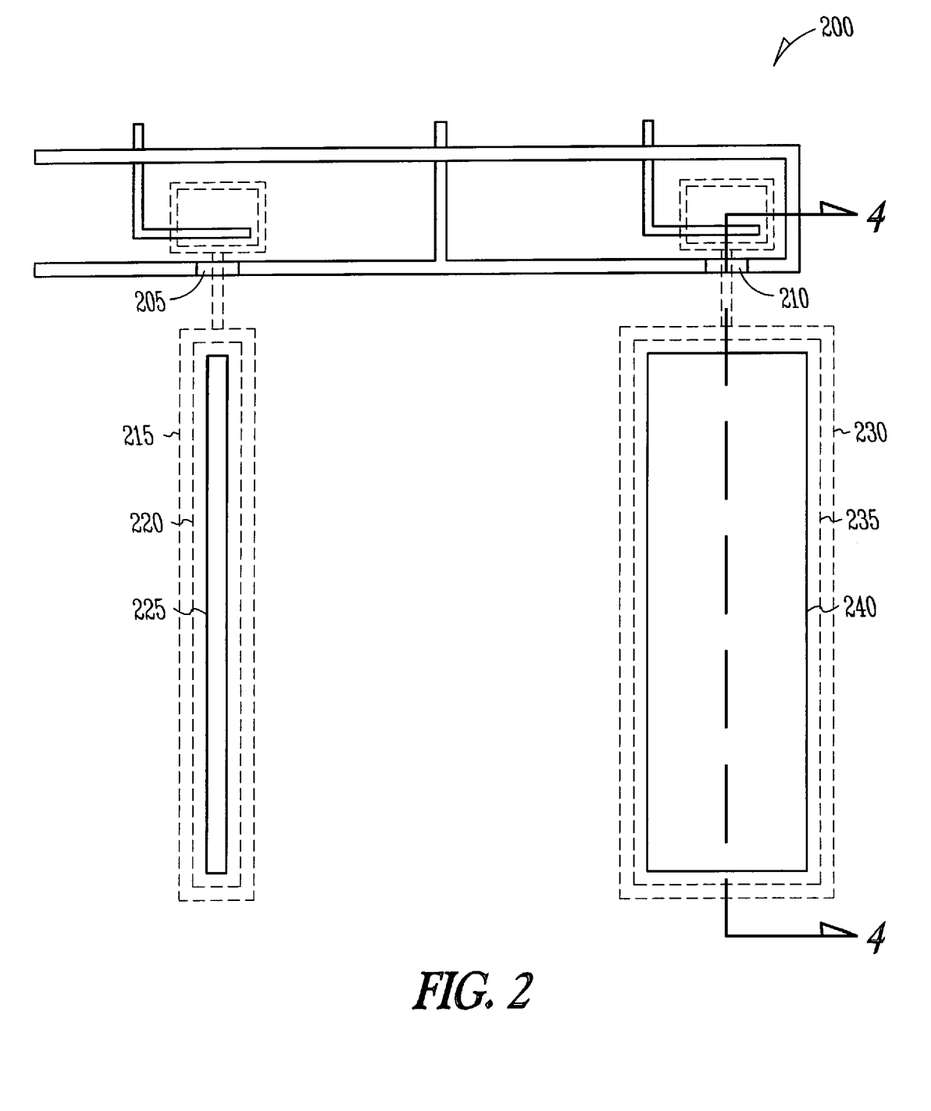
FIG. 2 is a block diagram of an EEPROM having extended floating gates according to an example embodiment.

FIG. 2 illustrates a device 200 that utilizes an EEPROM device 205, 210 to monitor the threshold voltage. A first extended floating gate is shown at 215, with a sensing gate 220 having an electret polymer coating an oxide etch window 225. A second extended gate is shown at 230, with a sensing gate 235 having an electret polymer coating an oxide etch window 240. The surface area of the second extended floating gate 230 is much larger than the surface area of the first extended floating gate 215. In one embodiment, the width of the second extended floating gate is larger than approximately 50 μm. The device 200 may be fabricated through a MOSIS (Metal Oxide Semiconductor Implementation Service) foundry with a 2-polysilicon and 2-metal process. Different poling methods may be used for devices with different sensing gate areas. Due to the fast and sensitive extraction, real-time monitoring of poling characteristics can be obtained.

Figure 3:
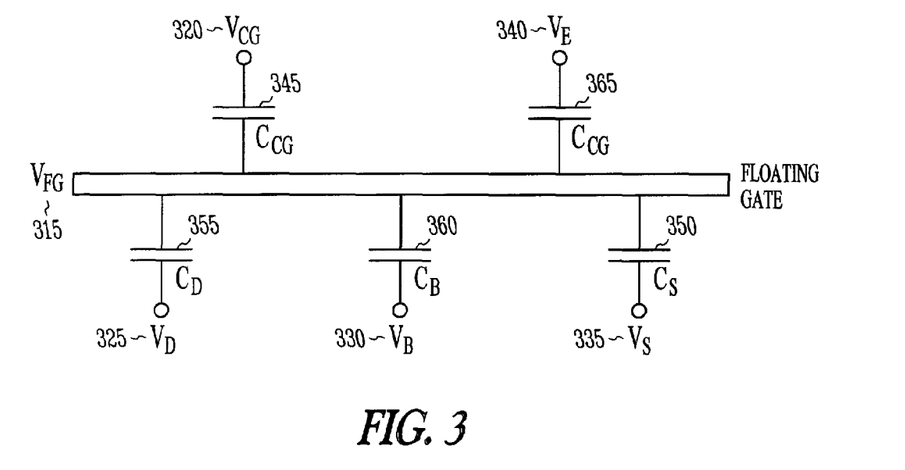
FIG. 3 is a diagram of a capacitor divider model for the EEPROM device of FIG. 2 according to an example embodiment.

FIG. 3 illustrates a capacitor-divider model for the EEPROM device 200 of FIG. 2. A floating gate 310 is connected with many input nodes through different dielectric layers, which is the same as the parallel connection of capacitors from the nodes as illustrated in FIG. 3. The net charge in the floating gate is the sum of the charge in each capacitor. $V_{FG}$ at 315 is the floating-gate potential. $V_{CG}$ 320, $V_D$ 325, $V_B$ 330, and $V_S$ 335 are the input signal voltages of control-gate, drain, substrate, and source, respectively. $V_E$ 340 is effective potential on the sensing gate set by the polymer electret film. $C_{CG}$ 345, $C_S$ 350, $C_D$ 355, $C_B$ 360, and $C_E$ 365 are the capacitive coupling coefficients between the floating gate and each of the input nodes. Let $Q_{FG}$ denote the net charge in the floating gate, $$Q_{FG} = C_{CG}(V_{FG}-V_{CG}) + C_E(V_{FG}-V_E) + C_D(V_{FG}-V_D) + C_B(V_{FG}-V_B) + C_S(V_{FG}-V_S). \quad (1)$$

If it is assumed that no charge injection occurs during IV measurements, then $Q_{FG}$ is equal to the initial charge on the floating gate, which may be taken as zero at the moment for simplicity. If voltages are measured with respect to the grounded substrate with the source and the substrate being shorted, equation (1) reduces to $$V_{FG} = \frac{C_{CG}V_{CG} + C_E V_E + C_D V_D}{C_{TOTAL}}, \quad (2)$$

where $$C_{TOTAL} = C_{CG} + C_E + C_D + C_B + C_S. \quad (3)$$

$V_{FG\_TH}$ and $V_{CG\_TH}$ are denoted as the threshold voltages of the EEPROM seen from the floating gate and the control gate, respectively. The EEPROM turns on at the condition of $V_{FG} > V_{FG\_TH}$, namely $$\frac{C_{CG}V_{CG} + C_E V_E + C_D V_D}{C_{TOTAL}} > V_{FG\_TH}. \quad (4)$$

Equation (4) is rearranged for $V_{CG}$ as $$V_{CG} > \frac{C_{TOTAL}}{C_{CG}} V_{FG\_TH} - \frac{C_E}{C_{CG}} V_E - \frac{C_D}{C_{CG}} V_D. \quad (5)$$

Before poling, there is no effective charge in the polymer film. Thus, the initial $V_{CG\_TH}^i$ is given by $$V_{CG\_TH}^i = \frac{C_{TOTAL}}{C_{CG}} V_{FG\_TH} - \frac{C_D}{C_{CG}} V_D. \quad (6)$$

After poling, charges are injected to the polymer film or dipoles in the film are polarized. If $Q_E$ is the total effective charges seen at the surface of the sensing gate, according to the Poisson equation, it will affect the potential of the floating gate by the capacitive coupling. Therefore, $V_{FG\_TH}$ in equation (6) shifts to $V_{FG\_TH} - Q_E/C_{TOTAL}$ after poling. Correspondingly, $V_{CG\_TH}^i$ shifts to $V_{CG\_TH}^f$ as $$V_{CG\_TH}^f = \frac{C_{TOTAL}}{C_{CG}} \left( V_{FG\_TH} - \frac{Q_E}{C_{TOTAL}} \right) - \frac{C_D}{C_{CG}} V_D \quad (7)$$

$$= \frac{C_{TOTAL}}{C_{CG}} V_{FG\_TH} - \frac{Q_E}{C_{CG}} - \frac{C_D}{C_{CG}} V_D.$$

The effective charge density $\rho_E$ in coul/cm² of the electret film can be obtained from (6) subtracted by (7):

$$\rho_E = Q_E/A_{SG} = -\Delta V_{CG\_TH} C_{CG}/A_{SG} \quad (8)$$

where $A_{SG}$ is the area of the sensing gate.

Figure 4:
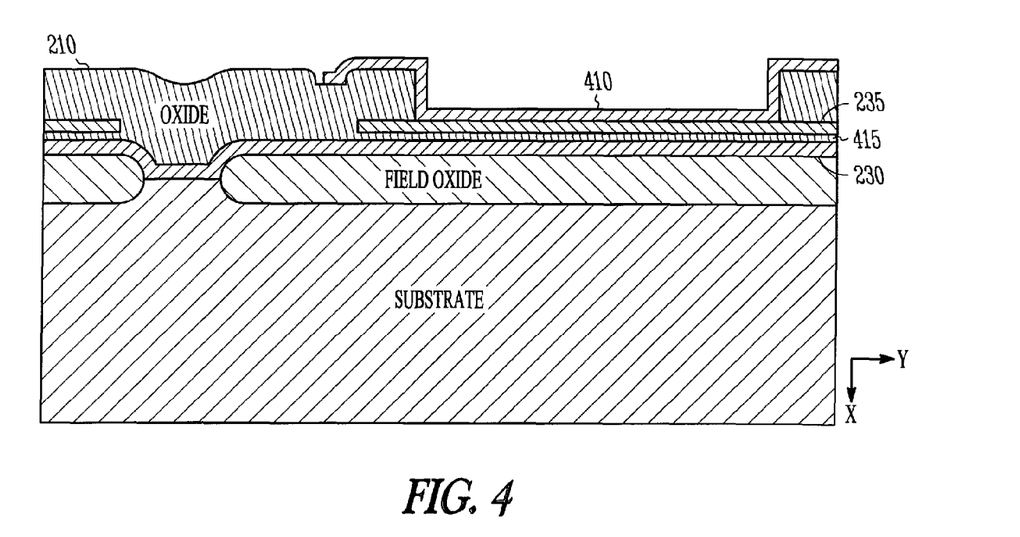
FIG. 4 is a cross section o the EEPROM of FIG. 2 taken along line 4-4.

FIG. 4 is a cross section of EEPROM 210 with extended floating gate 230 taking along lines 4-4 in FIG. 2. EEPROM 210 has n-type source and drain with a large extended floating gate 230, which provides amplified capacitive coupling to the sensing gate 235. An oxide etch window as a post-processing step is applied to remove a passivation layer on top of the sensing gate. Two different extended gate areas in FIG. 2 are employed to decouple the parasitic elements. In one embodiment, the large sensing gate 235 has an area of approximately 28,800 μm², which is ten times larger than the small one. Even smaller areas may be used in further embodiments.

Post-processing of a polymer coating as illustrated at 410 can be done either by direct attachment from pre-made solid polymer films or by dip-coating from polymer solutions. In one embodiment, an insulator is formed on top of the control gate, extended floating gate and sensing gate, and the oxide is removed over a portion of the sensing gate to allow contact with the polymer electret sensing coating. The portion of removed oxide may also serve as a portion of a channel for a microfluidic channel to deliver fluid which may contain chemicals to be sensed, or for sensing the pressure exerted by the fluid. A cover may be attached to complete the channel.

In further embodiments, the film may be a thin film, or may fill up the depression in the oxide shown in FIG. 4. In the dip-coating method, a Teflon® AF (polytetrafluoroethylene amorphous fluoropolymer) solution is 400S, provided by DuPont. The drying step is by a hot plate at 130° C. to evaporate the FC75 solvent from 3M. The Teflon film thickness is measured by a profilometer at 60 nm. This is just one example of a process of applying a polymer electret film. Many other methods may be used to obtain coating of desired films of varying thickness. In FIG. 4, the polymer coating is an electret that is directly coupled to the sensing gate 235. The sensing gate 235 is capacitively coupled to the extended floating gate 230 through a dielectric, such as an oxide layer 415.

Chemical Sensing in Solution

Without a function specific coating, the IV responses already show distinctive characteristics in different base solutions where the surface site adsorption (and hence $\phi_{OHP}$) will affect the threshold voltage $V_{TH}$ and the sensing-gate capacitance $C_{SG}$ will affect the substhreshold slope S. By various polymer coatings and charge conditions on the floating gate, extracted $C_{SG}$ alone can be used to distinguish chemical concentration and chemical species, where selectivity in chemical mixture can be achieved from response surface plots, which can reduce the dependence for a fluid reference potential. An extracted $\phi_{OHP}$ vs. ion concentrations with uncharged floating gate should have a slope inversely proportional to the number of charge but independent of the chemical species and surface coating. When the floating gate is charged, however, the extracted $\phi_{OHP}$ is distinctive to the ion species and coating, which can be used for selectivity enhancement and electrowetting control.

Protein Sensing in Buffered Solution

Two sample proteins, BSA (bovine serum albumin) and lysozyme are used to demonstrate the molecular sensing capabilities in one example. The proteins are denatured with SDS (sodium dodecyl sulfate), which causes the proteins to unfold by wrapping around the polypeptide backbone. SDS binds to the backbone with a mass ratio of 1.4:1, and in this way confers a negative charge to the protein in proportion to its mass. BSA and lysozyme are robust proteins that have significantly different masses of 66.2 kDa and 14.4 kDa, respectively. The difference in masses leads to differences in external net charge and, in turn, to differences in the $\phi_{OHP}$ and $C_{DIF}$ of the CvMOS device. Distinctive charge and capacitive responses can be observed from the two different molecules when the floating gate is charged with electron injection.

Pressure Sensing with Polarized Polymer Coating

When the sensing gate is coated by a material whose effective polarization changes with pressure, CvMOS can serve as a pressure sensor. A wide range of sensitivity can be achieved by selecting the pressure effects. Teflon AF, polarized by a poling electrical stress, is used for illustration where the sensitivity is in the 10 kPa range. In a further embodiment, mechano-poling is done by applying mechanical pressure on Teflon AF that has gone through photo-poling. The original amorphous Teflon is not piezoelectric due to lack of long-range directional order of charge density. However, if Teflon already contains significant space charges, it will demonstrate pressure responses from mechanical strain. For the same characterization structure, a mechanical pressure effect can be accurately determined, which may be used as a charge-based pressure sensor.

By using a piezoelectric coating on the sensing gate, the sensor device can function as a pressure sensor with a large tuning range. To enable both current and voltage sensing, the piezoelectric material can be sandwiched between two metal layers, which can also be used as additional grounding electrodes to further stabilize the device response. Both inorganic (such as PZT) and organic (PVDF) piezoelectric coating can be used, depending on the range of pressure of interest. For biomedical applications, PVDF coating not only has the feasible range for sensing, but also can be implemented in a flexible electrode.

By using a pyroelectric coating on the sensing gate, the sensor device can function as a temperature sensor. Most pyroelectric materials also demonstrate piezoelectric responses, and the individual contribution from the pressure and heat can be decoupled from two or more sensing gate with either different coating materials, or different thickness of the same pyroelectric/piezoelectric material.

Light Sensing with Photovoltaic Polymer Coating

Light sensing by CvMOS can be achieved with P3HT photovoltaic polymer coating. The polarization of P3HT and hence the IV changes depend on the wavelength and intensity. Different light sources thus give distinctive IV responses in FIG. 13. Notice that this is not due to the enhanced leakage of floating gate charges as the IV curve will quickly revert back to the one of charged FG with no light when the light is turned off. Detailed wavelength responses can also be obtained.

In one embodiment, electret charging involves photo poling by UV light with high DC biases. UV lamps were used to produce 8 W of one of the 254/302/365 nm wavelengths, which is located near the sample on a probe station. A plate probe of high voltage during the photo poling is located directly on the polymer film surface and the ground is connected to the substrate. This setup will put a large electric field across the electret polymer film. Further UV illumination will excite electrons and holes in the insulating polymer film traveling in opposite directions by the applied electric field. Some carriers can go out of the external surfaces of the polymer film and the others can be trapped to form space charge.

The effect of UV irradiation has been verified by applying transparent ITO (Indium-tin Oxide) contacts on the electret film, and found that the electric field uniformity is not a critical factor in photo poling. Dipole polarization can also result from different electron and hole transport properties. Photoelectret equilibrium charge density is mainly governed by the polarizing field intensity, which can be estimated by the product of light intensity and time of polarizing. The samples are erased by 254 nm UV light of 1.6 W for an hour without applied electric fields before all poling tests, which serves as the reference in obtaining threshold voltage difference.

The results from representative tests with different poling conditions show the range and sensitivity of the described characterization method. The size difference of the extended gate area is used to de-embed the intrinsic parasitic elements and to obtain a larger range of effective electret charge per unit area.

Figure 5:
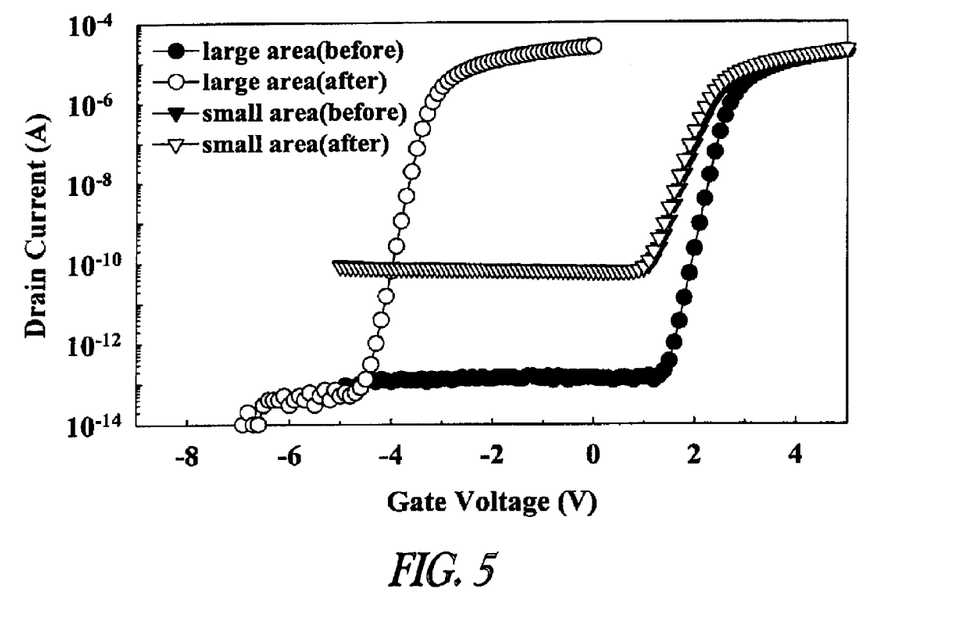
FIG. 5 illustrates typical threshold voltage characteristics for different EEPROMs according to an example embodiment.

FIG. 5 shows typical threshold voltage characteristics of two EEPROMs with 302 nm UV and a 200V poling voltage. The threshold shifts over a large range and after photopoling. Other alternative poling processes may include pressure poling and corona charging. With the same charge density in the polymer film, $\Delta V_{CG\_TH}$ with the larger sensing gate area is bigger according to Eq. (8). However, $\Delta V_{CG\_TH}$ is not exactly proportional to the ratio of the extended gate areas because the small extended gate area has relatively large parasitic capacitance. $\Delta V_{CG\_TH}$ of the two EEPROMs under test are −6.0V and −0.10V. $C_{CG}$, a capacitance between the floating gate and the control gate is 0.368 pF. Thus, the charge densities $\rho_E$ are $7.66 \times 10^{-9}$ coul/cm$^2$ and $1.27 \times 10^{-10}$ coul/cm$^2$ of positive charges for the large and small sensing gates, respectively. The difference in charge density can be explained by the UV shadowing and film thickness variation in the smaller sensing gate. The anomalous high current in the deep subthreshold region ($V_{CG}<1.0V$) in the small sensing gate case is repeatable and does not appear before the Teflon coating.

Figure 6:
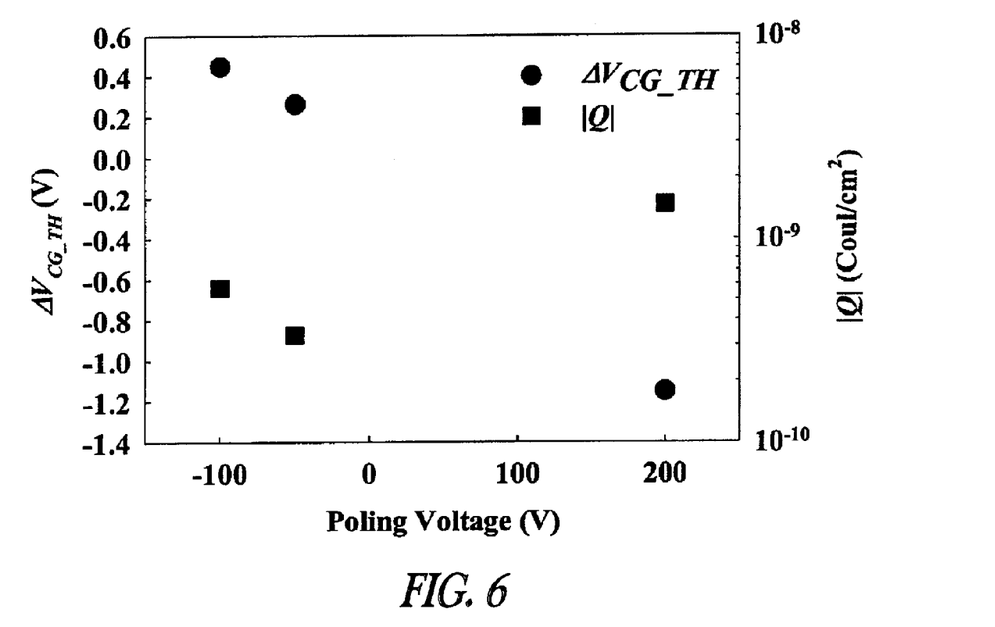
FIG. 6 illustrates typical threshold voltage characteristics for different EEPROMs according to an example embodiment.

FIG. 6 shows the threshold voltage characteristics of the EEPROM device with different poling voltages, −50V, −100V, and 200V. The changes of the threshold voltage are 0.448V, 0.262V, and −1.152V, respectively, which correspond to the charge densities $\rho_E$ in the polymer film as $-5.72 \times 10^{-10}$, $-3.35 \times 10^{-10}$ and $1.47 \times 10^{-9}$ coul/cm$^2$ respectively. The polarity and magnitude of the extracted charge density under different poling biases agree well with the expected values of the Teflon AF.

Figure 7:
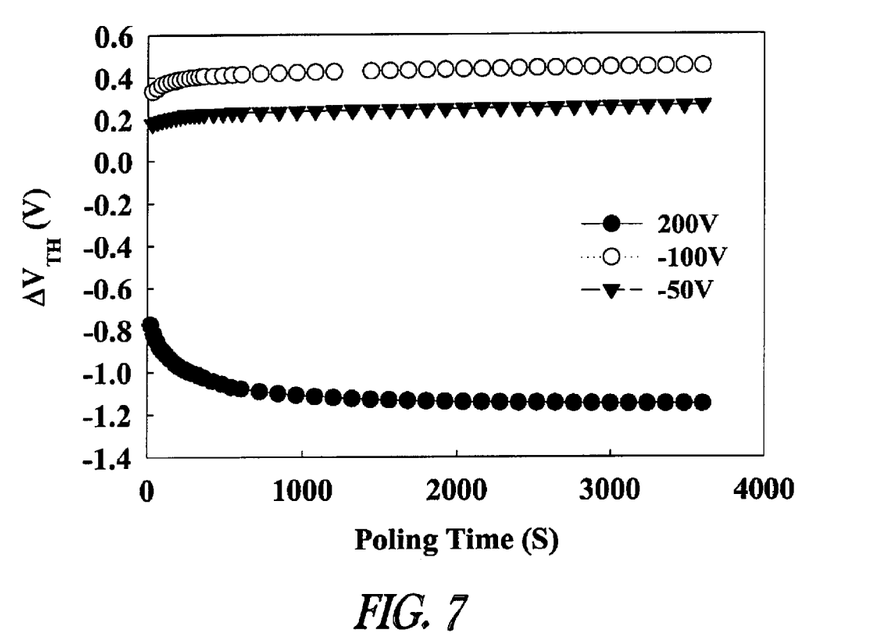
FIG. 7 illustrates time characteristics with different poling biases according to an example embodiment.

FIG. 7 shows the time characteristics of $\Delta V_{CG\_TH}$ with different poling biases. For 200V poling condition, the shift of the threshold voltage is saturated after 15 minutes poling application. For −50V and −100V, $\Delta V_{CG\_TH}$ saturates in 2-3 minutes. The effective charge density will saturate because the electric field within the electret film will decrease with the generation of static charges or charge dipoles during the poling process.

Figure 8:
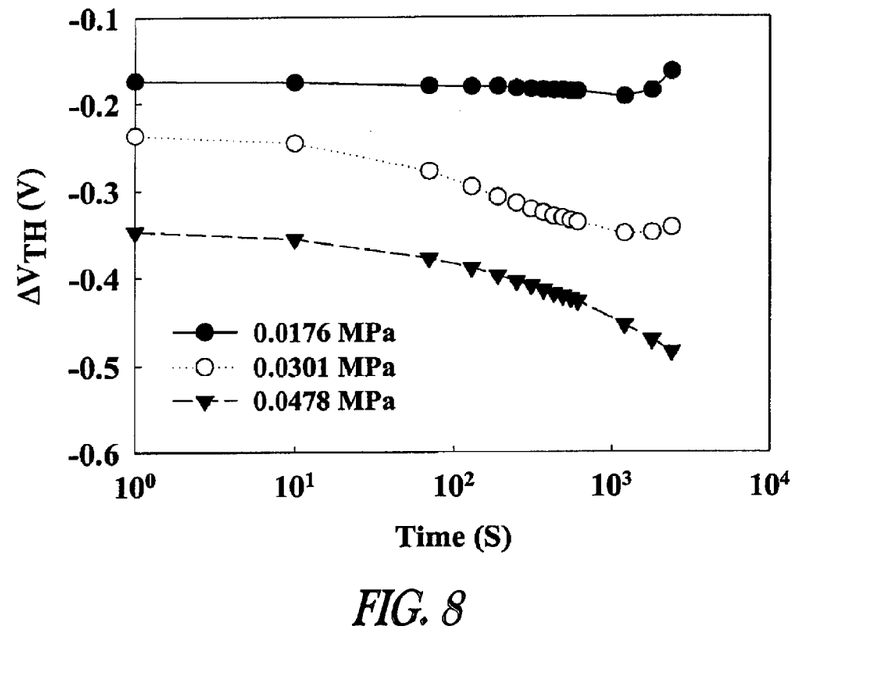
FIG. 8 illustrates measurement of a pressure effect according to an example embodiment.

FIG. 8 illustrates the measurements of a pressure effect. After UV erasure for reset and repeated charge injection by photo poling, the Teflon AF on the sensing gate is subject to mechanical pressure. The originally nonpolar Teflon AF film will be polarized after the photo poling process with residual charges, which will continuously change with further mechanical strain. FIG. 8 shows the time characteristics of $\Delta V_{CG\_TH}$ when pressure is applied to the Teflon AF film after the photo poling procedure. Although the initial response is instantaneous, there is a long-term drift that is either due to viscoelastic deformation or residual charges moving to the closest surface.

From FIG. 8 and Eq. (8), the changes of the threshold voltage of each pressure are −0.176V, −0.246V and −0.356V after 10 minutes of applied pressure. The effective charge densities are $2.25 \times 10^{-10}$ coul/cm$^2$, $3.14 \times 10^{-10}$ coul/cm$^2$ and $4.55 \times 10^{-10}$ coul/cm$^2$ of positive charges for 0.0176 MPa, 0.0301 MPa, and 0.0478 MPa, respectively.

The use of an electret on an extended floating gate of a transistor provides a charge based approach to sensing multiple different parameters on a single substrate. The use of a polymer electret allows for post circuit processes to form a multitude of different sensors by using different polymers that are compatible with the formed circuitry.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention claimed is:

1. A sensor comprising:
a field effect transistor having a source, drain, a control gate and floating gate, wherein the floating gate has an extended portion extending away from the control gate;
a sensing gate capacitively coupled to the extended portion of the floating gate; and
a polymer electret sensing coating electrically coupled to the sensing gate, wherein the polymer electret sensing coating comprises a piezoelectric coating that changes charge conditions on the floating gate responsive to pressure, wherein the piezoelectric coating includes a programmed bias charge.

2. The sensor of claim 1 wherein the piezoelectric coating changes charge conditions on the floating gate responsive to absolute pressure and wherein the control gate is adapted to set a bias point.

3. The sensor of claim 1 wherein the floating gate is charged.

4. The sensor of claim 1 wherein the extended floating gate has an area of approximately 28,800 µm$^2$ or less.

5. The sensor of claim 1 wherein the piezoelectric coating selected from the group consisting of PZT and PVDF.

6. A sensor comprising:
a field effect transistor having a source and drain formed in or supported by a substrate with a tunnel oxide separating the source and drain, a control gate formed substantially over the tunnel oxide and partially over the source and drain, and a floating gate formed between the tunnel oxide and control gate, wherein the floating gate has an extended portion extending away from the control gate;
a sensing gate capacitively coupled to the extended portion of the floating gate; and
a polymer electret sensing coating electrically coupled to the sensing gate, wherein the polymer electret sensing coating comprises a piezoelectric coating that changes charge conditions on the floating gate responsive to pressure, wherein the piezoelectric coating includes a programmed bias charge.

7. The sensor of claim 6 and further comprising an insulator formed on top of the control gate, extended floating gate and sensing gate, and wherein the oxide has been removed over a portion of the sensing gate to allow contact with the polymer electret sensing coating.

8. The sensor of claim 6 wherein the piezoelectric coating is selected from the group consisting of PZT and PVDF.

9. The sensor of claim 6 and further comprising multiple sensors formed in or supported by the substrate.

10. A method comprising:
exposing an electret sensing coating comprising a piezoelectric coating of a CvMOS transistor sensing gate to pressure, such that the pressure causes a change in charge density in the electret sensing coating;
capacitively coupling the electret sensing coating to an extended portion of a floating gate;
changing a potential on a floating gate of an EEPROM device using a control gate of the CvMOS transistor such that a threshold voltage of the EEPROM device is correlated to the electret charge density; and
programming the electret sensing coating using the control gate.

11. The method of claim 10 wherein programming the electret sensing coating comprises creating a bias charge in the electret sensing coating by applying a high voltage to the control gate.

* * * * *